United States Patent [19]

Lightle et al.

[11] Patent Number: 4,947,942
[45] Date of Patent: Aug. 14, 1990

[54] ANGLE DRIVE FOR A SURGICAL POWER TOOL

[75] Inventors: Paul S. Lightle, Kalamazoo; Lawrence R. Milks, Hickory Corners, both of Mich.

[73] Assignee: Stryker Corporation, Kalamazoo, Mich.

[21] Appl. No.: 304,567

[22] Filed: Jan. 31, 1989

[51] Int. Cl.⁵ ............................................. A61C 1/02
[52] U.S. Cl. .................................. 173/163; 74/417; 81/57.28; 464/157
[58] Field of Search ............ 173/163; 81/57.13, 57.28, 81/57.29, 57.31, 57.45; 464/106, 139, 141, 157, 158, 159; 384/610; 74/425, 416, 417

[56] References Cited

U.S. PATENT DOCUMENTS

| | | | |
|---|---|---|---|
| 807,452 | 12/1905 | Franke | 173/163 |
| 2,697,362 | 12/1954 | Keesling | 74/417 |
| 2,921,451 | 1/1960 | Helmke | 464/106 |
| 4,295,829 | 10/1981 | Martinelli et al. | 173/163 |

FOREIGN PATENT DOCUMENTS

| | | | |
|---|---|---|---|
| 15259 | of 1889 | United Kingdom | 464/157 |
| 461096 | 2/1937 | United Kingdom | 384/610 |
| 531258 | 1/1941 | United Kingdom | 384/610 |
| 578287 | 6/1946 | United Kingdom | 464/157 |

*Primary Examiner*—Frank T. Yost
*Assistant Examiner*—Scott A. Smith
*Attorney, Agent, or Firm*—Flynn, Thiel, Boutell & Tanis

[57] ABSTRACT

An angle drive for a surgical power tool comprises a tool housing and first and second shafts rotatably supported end to end in the housing. The shafts have rotational axes which cross at an obtuse angle. Interengaged, opposed bevel gears are provided on the adjacent ends of the shafts for rotating of one shaft by the other. A ball is received in coaxial, frustoconical recesses in the adjacent ends of the shafts to locate one shaft with respect to the other and determine the meshing clearances between the bevel gear teeth.

16 Claims, 5 Drawing Sheets

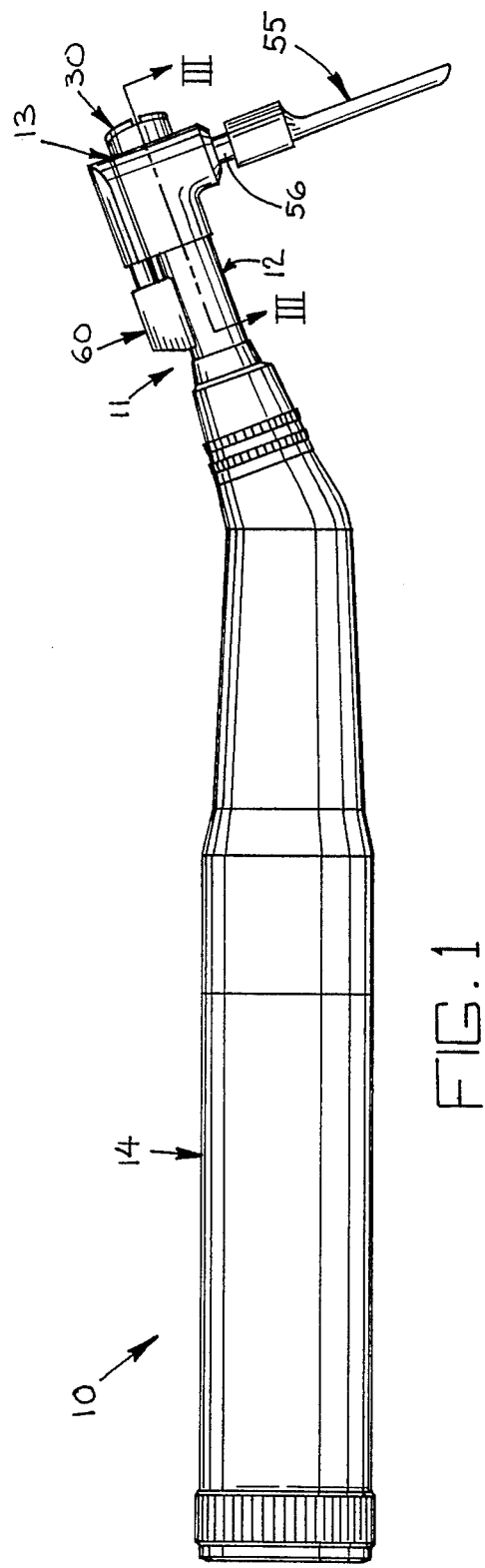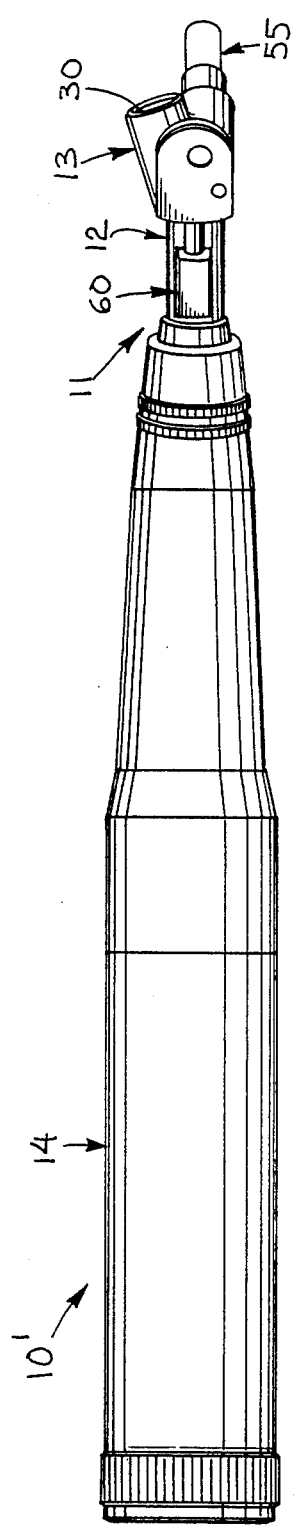

ANGLE DRIVE FOR A SURGICAL POWER TOOL

FIELD OF THE INVENTION

This invention relates to an angle drive for a surgical power tool, and more particularly to one in which first and second shafts are disposed end to end at an obtuse angle for driving one by the other.

BACKGROUND OF THE INVENTION

A surgical tool is known (for example the model number 296-17-40 manufactured by the assignee of the present invention) in which a worm is rotatably reversibly driven by an input shaft and in turn drives a worm gear for driving a tool, in which the worm shaft and input shaft are disposed end to end with their rotational axes at an obtuse angle and the input shaft drives the worm shaft through bevel gears mounted on the adjacent ends of the shafts. In a prior surgical tool provided with such an angle drive, rotational driving of the worm gear sets up axial thrust forces tending either to crush the bevel gears axially together or to axially separate them, depending on the direction of rotation of the worm. In a prior design, the axial forces tending to crush the bevel gears together are countered by a rigid outwardly extending annular shoulder on the worm shaft which, through a surrounding axial thrust bearing, is backed by a portion of the surgical tool housing. Unfortunately, the thrust bearing must be relatively large in diameter, compared to the shaft diameter, and hence is bulky and expensive. Further, the bearing must be capable of handling loads which, in view of its large diameter, are imposed at relatively high circumferential speeds. Under these conditions, a multielement, so-called low friction bearing (multiple ball or roller bearing) is called for, thus increasing the cost of the tool. Substitution of a simple single element face to face sliding bearing risks bearing heating and relatively rapid wear of the axially opposed, relatively rotating rubbing surfaces of the axially opposed, annular bearing faces.

Further, radial thrust bearing means are required, in order to maintain the rotational axis of the worm shaft fixed with respect to the rotational axis of the input shaft which drives it. Such increases the cost and complication of the above-described axle thrust bearing arrangement.

Further, relatively complex machining of the interior of the housing must be carried out with a relatively high degree of accuracy to correctly locate the mentioned thrust bearing coacting between the worm shaft and housing.

In addition, despite care taken to maintain close tolerances in the location of the bearing members on the housing and on the worm shaft, it is difficult to achieve, and more difficult to maintain over time, optimum clearances between coacting portions of the bevel gears on the adjacent ends of the two shafts, such that slight misalignment may readily occur, leading to excessive friction between, and wear on, the meshing bevel gears.

In addition, since the worm shaft may be driven in either rotational direction, the bearings must be arranged to handle axial thrust loads in either axial direction along the worm shaft, as well as radial loads thereon. This is particularly true in view of the driving by the worm shaft of a worm gear transverse thereto.

Accordingly, the objects and purposes of this invention include provision of an angle drive for a surgical power tool which is intended to overcome the above-described drawbacks associated with known obtuse angle drive surgical tools. The objects of the present invention further include provision of a surgical tool angle drive which reacts against the axial and radial loads applied to the shafts and bevel gears disposed therebetween while maintaining accurate alignment and positioning of the mesh of the bevel gears, which provides a low friction rolling contact having a circular line of contact with each shaft rather than the prior rubbing surface contact or complex multiple ball or roller bearing of prior devices, and which handles thrust loads on the rotating worm shaft at a relatively small bearing diameter for reducing tangential surface speeds at the bearings. The objects of the invention further include provision of a bearing structure which is mechanically very simple, which requires only relatively minor and easily implemented machining of the adjacent shaft ends, which eliminates the need for machining within the housing to accommodate the bearing mount surrounding the worm shaft, and which tends to allow the bevel gears on the respective shaft ends to float with respect to each other and thereby maintain proper clearances therebetween for a long service life and efficient transfer of motion.

Other objects and purposes of the invention will be apparent to persons of ordinary skill in this art upon reading the following description and inspecting the accompanying drawings.

BRIEF DESCRIPTION OF THE DRAWINGS

FIG. 1 is an elevational view of a surgical tool embodying the present invention.

FIG. 2 is a top view of the FIG. 1 tool.

SUMMARY OF THE INVENTION

Figure 3:
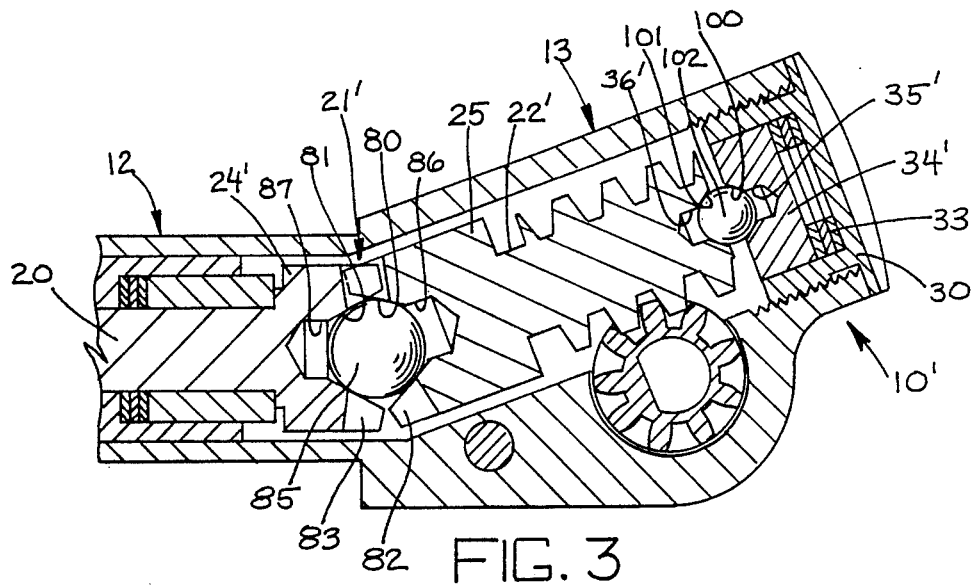
FIG. 3 is an enlarged fragmentary central cross-sectional view substantially taken on the line III—III of FIG. 1.

An angle drive for a surgical power tool comprises a tool housing and first and second shafts rotatably supported end to end in said housing, the shafts having rotational axes which cross at an obtuse angle. Interengaged, opposed drive elements are provided on the adjacent ends of the shafts for rotating of one shaft by the other. A ball received in coaxial recesses in adjacent ends of the shafts locates the shafts one with respect to the other.

DETAILED DESCRIPTION

A prior surgical power tool 10 (FIGS. 1 and 2) comprises a housing 11 having a handle 12 arranged at an obtuse angle with respect to a head 13. A drive motor 14 is housed in the handle 12. The motor 14 is here electrically powered, but a motor powered by other means (e.g. pressure fluid) may be used. Control of motor on-off and/or speed may be by any convenient means not shown. A chuck 15 carried by the head 13 is rotatably driven by the motor 14 at a desired speed and in turn drives a bit 55 of any desired kind chucked therein.

Figure 5:
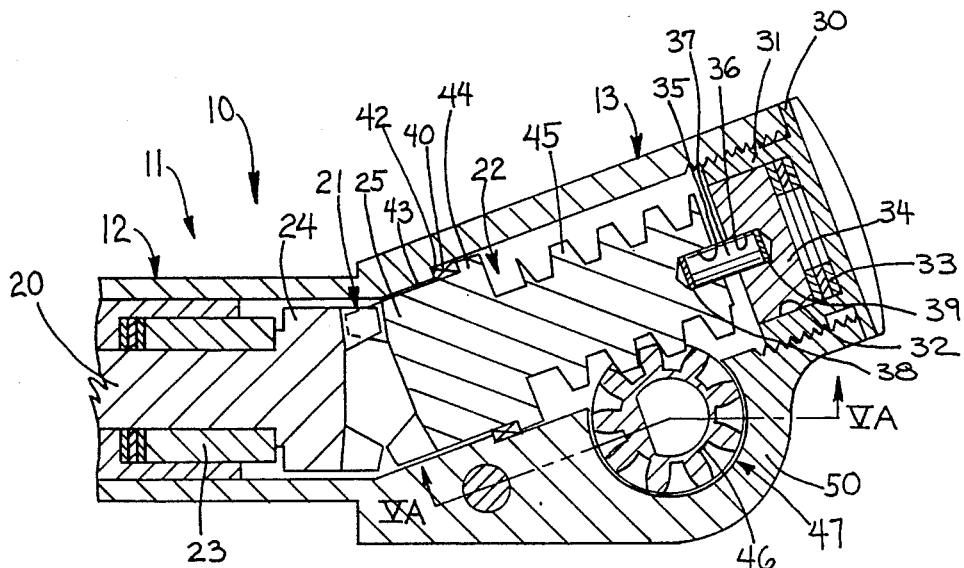
FIG. 5 is a view similar to FIG. 3 but showing a prior art structure.

To drive the chuck 15 from the motor 14, shaft means extend from the motor to the chuck and are rotatably supported within the housing 11 to rotatably drive the chuck from the motor. At the obtuse angle bend in the housing 11, the drive means is defined by a rotatable input shaft 20 (FIG. 5) which through a set of bevel gears 21 rotatably drives the adjacent end of a worm shaft 22. As seen in FIG. 5, the rotational axes of the input shaft 20 and worm shaft 22 are coplanar and intersect at an obtuse angle, corresponding to the obtuse angle of the housing 11. The input shaft 20 is fixed radially and axially and is supported for rotation by bearings adjacent its ends, the bearing adjacent its rightward end being indicated at 23 in FIG. 5.

The bearing 23 here is provided as a sleeve bearing fixed within the housing 11. The bearings associated with the input shaft 20 handle radial loads and rightward and leftward axial loads, so as to fixedly but rotatably locate the input shaft 20 in the housing 11.

The meshing bevel gears 21 protrude toward each other from enlarged diameter, adjacent ends 24 and 25 respectively of the input shaft 20 and worm shaft 22.

The rightward, free end of the head 13 is closed by a short, large diameter screw 30 (FIG. 5) having an externally threaded shank 31 threadedly received in the rightward end of the head 13. The screw 30 is generally cup shaped, the shank 31 being hollow and opening leftward toward the worm shaft 22 in coaxial relation therewith. The shank 31 thus has a central recess 32 opening leftward toward the worm shaft 22. Washerlike shims 33 of appropriate thickness are located in the rightward, bottom end of the central recess 32 to axially back and position a bearing support puck 34 in the rightward open end of the central recess 32 at a desired distance from the rightward end of the worm shaft 22.

In the tool 10 shown in FIGS. 1 and 5, the worm shaft 22 is supported for rotation in the head 13 as follows.

The opposed ends of the worm shaft 22 and puck 34 have opposed, coaxial, central bores 35 and 36. A bearing pin 37 is coaxially received in the opposed bores 35 and 36 and is rotatable with respect to at least one of the worm shaft 22 and puck 34, preferably the latter. Bearing disks 38 and 39 of suitable bearing material separate the ends of the pin 37 from the ends of the bores 35 and 36. The pin 37 resists axial compression loads as well as radial loads, and therefore locates the worm shaft 22 against rightward movement, as well as radial movement, with respect to the head 13.

At the left end of the worm shaft 22, a ring 40 (FIG. 5) of bearing material is fixedly surrounded by the interior peripheral wall 41 of the hollow head 13. The left end of the bearing ring 40 is axially backed by a rightward facing step 42 in a peripheral wall 41 of the head 13. The bearing ring 40 extends radially inboard of the step 42. The periphery 43 of the enlarged diameter portion 25 of the worm shaft 22 bears rotatably on the radially inner surface of the bearing ring 40. The enlarged diameter portion 25 at its rightward end has a radially outwardly extending flange 44 that clears the inner peripheral wall 41 radially but is backed axially by the rightward end of the bearing ring 40. In this way, the bearing ring 40 supports the leftward end of the worm shaft 22 for rotation and against leftward movement with respect to the head 13, and thus acts as a radial thrust, and leftward axial thrust, receiving bearing.

The pin 37 and bearing ring 40 thus radially and axially fix the location of the rotational axis of the worm shaft 22.

Figure 5A:
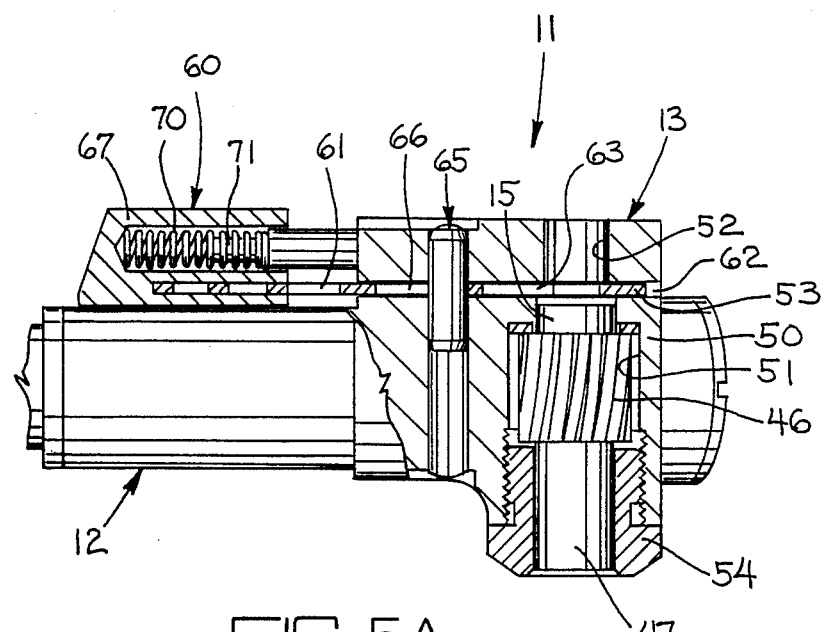
FIG. 5A is a fragmentary sectional view taken on the line VA—VA of FIG. 5.

The rightward end portion of the worm shaft 22 is provided with external teeth in the form of a worm 45. In driven mesh with the worm 45 is a worm gear 46 coaxially and fixedly located near the upper end of a worm gear shaft 47 (FIGS. 5 and 5A). The head 13 has a lateral bulge 50. The chuck 15 here comprises a D-cross section, coaxial hole 51 extending lengthwise through the worm gear shaft 47. The worm gear shaft 47 (FIG. 5A) is upwardly received in a downward opening recess 51 defining the bottom portion of a vertical through hole 52 in the bulge 50 of the head 13. The worm gear shaft 47 is axially and radially located for rotation in the bulge 50 by location of the worm gear 46 between a thrust washer 53 located thereabove at the blind end of the recess 51, and a thrust bushing 54 threaded (or press fitted) up into the bottom of the recess 51. A surgical bit 55 of any desired type is provided with a shank 56 and a base 57 contoured to be received in and rotatably driven by the chuck 15.

The bit 55 is releasably retained in the chuck 15 by any convenient means. In the prior tool 10 shown in FIG. 5A for example, a bit retainer 60 comprises a retainer plate 61 rightwardly/leftwardly slidable in a laterally opening slot 62 in the bulge 50 above the recess 51 and worm gear shaft 47. A hole 63 through the retainer plate 61 adjacent its rightward end communicates with the vertical through hole 52 and receives therethrough the shank 56 of the bit 55. More particularly, the portion of the retainer plate 61 bounding the rightward end of the hole 63 is, upon leftward movement of the retainer plate 61, engagable with an annular groove 61 just above the D-cross section base 57 of the bit shank 56 to lock the bit 55 vertically in place in the bulge 50. Rightward shifting of the retainer plate 61 releases the bit 55 from the bulge 50. To prevent the retainer plate 61 from dropping out of the slot 62, a vertical roll pin 65 seated in the bulge is received in a laterally opening notch 66 in the retainer plate 61, such that the roll pin 65 also defines the limits of leftward, rightward movement of the retainer plate 61 in the bulge 50. The retainer 60 also includes a slide block 67 slidably longitudinally along the top of the handle 12 and fixed to the leftward end of the retainer plate 61. The retainer 60 is resiliently urged leftwardly with respect to the head 13 by a spring 70 received in a rightwardly opening recess in the slide bar 67 and sleeved over the reduced diameter leftward end 71 which extends fixedly from the leftward end of the bulge 50. Thus, manual sliding of the slide block 67 rightwardly against the force of the spring 70 disengages the periphery of the hole 63 from the groove 64 in the surgical bit 55 to release the bit from the head 13. On the other hand, manual release of the slide block 67 allows the spring 70 to bias it and the retainer plate 61 leftward sufficient to cause the retainer plate at the rightward end of the hole 63 to engage in the groove 64 of a bit 55 located in the chuck 15, to retain the bit 55 in the chuck 15.

To the extent above described, the tool 10 is conventional and is disclosed as one example of a surgical tool to which the present invention is applicable. It will however be understood that the present invention is applicable to a variety of other surgical tools (including dental tools) in which shafts meet end to end at an obtuse angle to transfer motion, particularly pivotal or rotary motion.

Figure 3A:
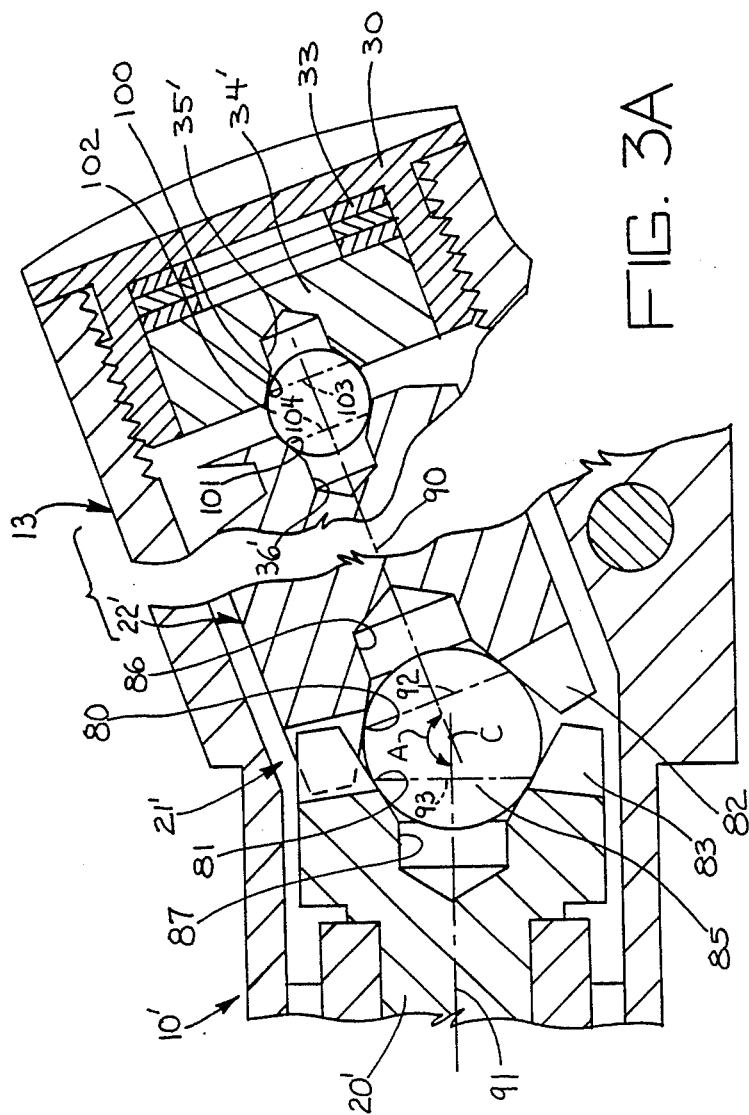
FIG. 3A is an enlarged fragment of FIG. 3.
Figure 4:
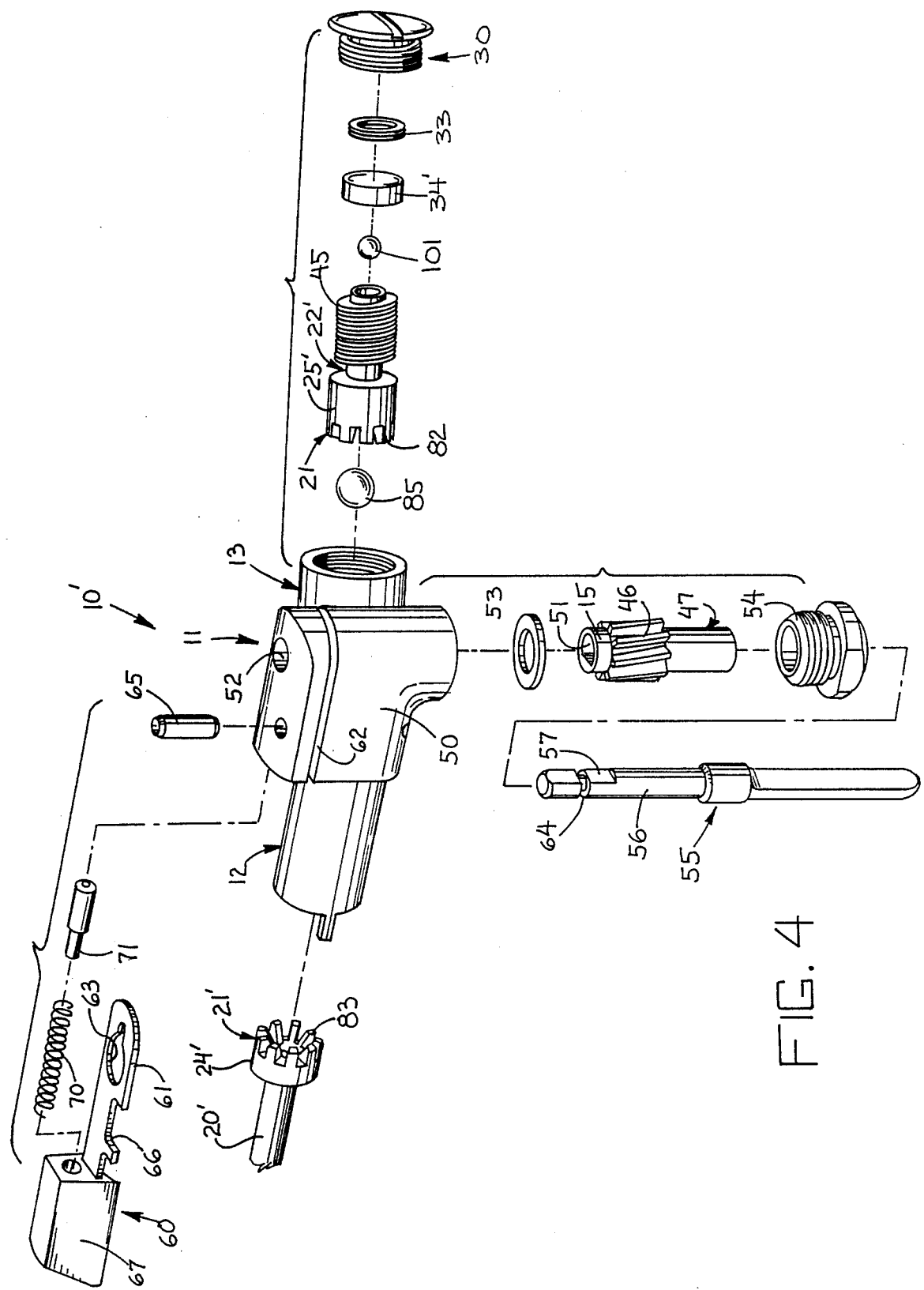
FIG. 4 is an exploded view of the structure of FIG. 3.

Turning now to portions of the disclosed structure more specifically defining the present invention, attention is directed to the tool 10' of FIGS. 3, 3A and 4.

As seen in FIGS. 3, 3A and 4, the present invention eliminates the thrust bearing ring 40, radial flange 44 and bearing pin 37 of prior FIG. 5.

Under the present invention, the worm shaft 22' and input shaft 20' are provided at their opposed ends with respective frustoconical recesses 80 and 81. The recesses 80 and 81 are respectively coaxial with the shafts 22' and 20'. The frustoconical recesses 80 and 81 continue through the axial extent of the teeth 82 and 83 of the set of bevel gears 21'.

A large diameter bearing ball 85 is snugly but rotatably received in the opposed frustoconical recesses 80 and 81. The bottoms of the frustoconical recesses 80 and 81 are relieved by coaxial bores 86 and 87 which respectively extend axially into the shafts 22' and 20' from the blind end of the respective frustoconical recesses 80 and 81. Thus, the central, rotational axes 90 and 91 (FIG. 3A) of the shafts 22' and 20' cross at the center C of the ball 85. The bearing ball 85 engages the shafts 22' and 20' along respective circular lines of rolling contact shown in broken lines at 92 and 93.

In one unit constructed according to the invention, the diameter of the enlarged portions 24' and 25' of the shaft 22' or 20' (i.e. the diameter of the shaft at the root of the teeth 82 or 83) was about 1.7 times the diameter of the ball 85. However, it is contemplated that the shaft diameter may be between 1.5 and 1.9 times the ball diameter. In the same unit constructed according to the invention, the diameter of the ball 85 was about 0.109 inches.

In one unit constructed according to the invention, the angle of the sidewall of the frustoconical recess 80 or 81 to the central axis 90 or 91 of the corresponding shaft was about 30°, although an angle in the range of about 15° to 45° is contemplated.

In one unit constructed according to the invention, the obtuse angle A between the shaft axes 90 and 91 was about 160°, although angles in the range between 135° and 180° are contemplated.

The rightward end of the worm shaft 22' and the puck 34' have aligned, coaxial bores 35' and 36', which may be more or less similar in size to the bores 35 and 36 above discussed with respect to FIG. 5. However, the bores 35' and 36' are widened at their opposed open ends to form respective, preferably identical, frustoconical recesses 100 and 101 (FIG. 3A). The angle of the wall of the frustoconical recesses 100 and 101 to the axis 90 of the worm shaft may be similar to that above described with respect to the frustoconical recesses 80 and 81. A bearing ball 102, similar to but smaller than the bearing ball 85, is disposed in the frustoconical recesses 100 and 101 in rolling contact with the puck 34' and shaft 22'. The ball 102 engages the puck 34' and shaft 22' along respective annular lines of contact indicated in broken lines at 103 and 104.

The input shaft 20' is rotatably supported in an axially and radially fixed position within the housing in the manner above described with respect to input shaft 20 of FIG. 5. The balls 85 and 102 and worm shaft 22' are axially trapped between the frustoconical recess 81 in the input shaft 20' and the frustoconical recess 100 in the puck 34'. The balls 85 and 102 are radially trapped by the frustoconical walls of the recess pairs 80, 81 and 103, 104. The balls 85 and 102 are snugly located in their respective frustoconical recess pairs. Accordingly, the radial and axial location of the worm shaft 22' is accurately defined via its contact with the balls 85 and 102.

The axial clearance between the shafts 20' and 22', the balls 85 and 102, and the puck 34' is set by the thickness of the shims 33 axially trapped between the puck 34' and the closed outer end of the screw 30 due to the slope of the walls of the frustoconical recesses 80, 81 and 100, 101. The axial clearance above mentioned thus determines the radial clearance in axially and radially locating the worm shaft 22'. The balls 85 and 102 also determine the clearance between the bevel gear teeth 82 and 83.

In rotatably driving the worm gear shaft 47 the worm shaft 22' is subject to a net rightward or leftward axial thrust, depending on the direction of rotation thereof, due to the rotational resistance of the worm gear shaft 47. The balls 85 and 102 resist the resulting compressive axial thrust applied thereto.

The radial location of the worm shaft 22' defined by the clearance thereof with respect to the balls 85 and 102 also determines the tooth clearance between the worm 45 and worm gear 56 (FIG. 4).

The larger diameter of the ball 85, as compared to the ball 102, compensates for the higher thrust loads applied to the ball 85 by reason of the non-coaxial alignment of the shafts 20' and 22', and by reason of the reduction in contact surface of the shafts with the ball 85 due to the fact that the rolling contact circles 92 and 93 on the ball 85 are circumferentially incomplete. The incompleteness results since the ball 85 contacts the shafts on the radially inner portions of the teeth 82 and 83, although such contact is near the roots of such teeth, and the shaft to ball contact is greater than it would be if the ball contacted the teeth closer to their free ends (tips). Also, more torque and resulting compressive bearing loads are encountered on this ball 85 in the forward (and consequently cutting) direction of the tool, thereby requiring a larger ball at 85 than on the other end of the shaft 22' that reacts loads of smaller magnitude encountered when running the tool in reverse.

To assemble the inventive tool 10' shown in FIG. 3A, the input shaft 20' is radially and axially fixedly located within the housing. The ball 85 and worm shaft 22' and ball 102 can then be inserted axially, one after the other, into the open rightward end of the head 13 and then fixedly located by threadedly inserting the screw 30, with the puck 34' and the proper thickness of shims 33 within the recessed leftward end of the screw 30. The thrust washer 53 and worm gear shaft 47 and thrust bushing 54 can then be axially inserted up into the bulge 50 in the manner above discussed with respect to conventional FIG. 5A.

Removal of the worm shaft 22' and its bearings (namely the balls 85 and 102) is accomplished by reversal of these steps. Thus, the balls 85 and 102, and the worm shaft 22' can very easily and quickly be replaced if need be.

During assembly the balls 85 and 102 and worm shaft 22' in effect float into position, so that there is no need to guide the worm shaft 22' axially into snug fitting radial bearings as in the prior art device above described with respect to FIG. 5.

Moreover, after a long period of use, should the balls 85 and 102, or the contact surfaces on the shafts 20' and 22' and puck 34' become worn, at some degree of wear can be accommodated by replacing the shims 33 with somewhat axially thicker shims.

In operation, it will be seen that the relative speed between the left end of the worm shaft 22' and its supporting ball 85 will be substantially less than the circumferential speed differential between the prior art shaft 22 and its surrounding thrust bearing ring 40. This is due to the reduced contact diameter between shaft and bearing and due to the substantially reduced relative rotation speeds of the ball 85 and shaft 22' (normally the ball 85 will rotate to some extent with respect to both of the shafts 20' and 22') under the present invention as shown in FIG. 3A. This substantial reduction in relative tangential speeds between bearing and shaft should reduce heat generation at the bearing and increase service life by reducing wear.

Moreover, the same factors should reduce the rolling resistance on the shaft 22' and thus, at least to some extent, increase power transmission efficiency between the input shaft 20' and the worm gear shaft 47 (FIG. 4).

Although the inventive bearing arrangement of FIG. 3A was initially applied to relatively high speed surgical power tools, namely tools with worm shaft 22' speeds of about 17,500 RPM, the inventive bearing arrangement is considered to be usable at a wide variety of rotative speeds, for example in the range of 0 to 60,000.

While it is contemplated that the balls 85 and 102, and shafts 20' and 22' can be of a variety of materials, in one unit constructed according to the invention, and found to be successful operationally, the balls 85 and 102 were of 440 c stainless steel, and the shafts 20' and 22' were of 440 c stainless steel.

Although the balls 85 and 102 are discussed above as being located in the cone shaped recesses 80, 81 and 100, 101, it is contemplated, within the broader aspects of the invention, that recesses of spherical shape may instead be provided for receiving one or both of the balls 85 and 102.

Although a particular preferred embodiment of the invention has been disclosed in detail for illustrative purposes, it will be recognized that variations or modifications of the disclosed apparatus, including the rearrangement of parts, lie within the scope of the present invention.

The embodiments of the invention in which an exclusive property or privilege is claimed are defined as follows:

1. An angle drive for a surgical power tool, comprising:
   a surgical tool housing;
   driving and driven shafts rotatably supported end to end in said housing, said shafts having rotational axes which cross at an obtuse angle;
   means for fixedly positioning said driving shaft for rotation in said housing;
   means for rotatably driving said driving shaft;
   opposed bevel gears on the adjacent ends of said shafts, said bevel gears being enmeshed for driving said driven shaft from said driving shaft;
   means for driving a surgical bit from said driven shaft;
   means rotatably supporting said driven shaft in said housing, said driven shaft supporting means including means piloting the adjacent end of said driven shaft on the adjacent end of said driving shaft, said piloting means comprising opposed recesses disposed coaxially in the adjacent ends of said shafts and a ball received in said recesses in said shafts and being sandwiched for relative rotation between the adjacent ends of said shafts, said recesses being conical, said ball contacting the wall of each said recess with only a line contact, said conical recesses each continuing axially and radially outward to form the radially inner faces of teeth of the opposed bevel gears, said line contact being circular and extending along said radially inner faces of said teeth of the corresponding bevel gear such that the contact line of each recess with the ball is circumferentially broken by gaps between the teeth of the corresponding bevel gear, the diameter of said ball exceeding the diameter of a said recess at the roots of the corresponding bevel gear teeth.

2. The apparatus of claim 1 in which the shaft diameter at the root of said bevel gears is between 1.5 and 1.9 of the ball diameter.

3. The apparatus of claim 2 in which the shaft diameter at the root of said bevel gears is about 1.7 times the ball diameter.

4. The apparatus of claim 1 in which the side recess is at about 20 degrees to 40 degrees from the axis of said recess.

5. The apparatus of claim 4 in which the cone angle is about 30 degrees.

6. The apparatus of claim 1 in which the bottoms of said conical recesses are relieved so as not to contact said ball.

7. The apparatus of claim 1 including means preventing axial movement of said driven shaft away from said driving shaft.

8. The apparatus of claim 7 in which said preventing means comprises a second ball sandwiched between the remote end of said driven shaft and an opposed fixed part of said housing, said second ball being coaxial with said driven shaft, aid first ball being substantially larger than said second ball.

9. The apparatus of claim 8 in which said second ball is received in coaxial frustoconical recesses in said remote end of said driven shaft and in said opposed fixed part of said housing.

10. The apparatus of claim 9 in which said frustoconical recesses are relieved centrally so that the second ball has only a circular line contact with said driven shaft and said housing.

11. The apparatus of claim 8 in which said first mentioned ball is between 1.5 and 1.9 times the diameter of said second ball.

12. The apparatus of claim 11 in which said first mentioned ball is about 1.7 times the diameter of said second ball.

13. The apparatus of claim 1 in which said means for rotatably driving a tool from said driven shaft comprises a rotatable worm gear with an axis extending transverse to the axis of said driven shaft, said driven shaft having fixed thereon a worm intermediate the ends thereof and in rotatably driven mesh with said worm gear so as to be rotatably driven thereby.

14. The apparatus of claim 13 in which the rotational axes of said shafts define a plane, the longitudinal axis of said worm being substantially perpendicular to said plane.

15. The apparatus of claim 14 in which said worm is disposed on the side of said driven shaft opposite said obtuse angle.

16. An angle drive for a surgical power tool, comprising:
   a surgical tool housing;

a driving shaft rotatably fixedly supported in said housing, a driven shaft in said housing, said shafts having rotational axes which intersect at an obtuse angle;

means for rotatably driving said driving shaft;

output means positively driven by said driven shaft for driving a surgical bit;

means positively driving an input end of said driven shaft from said driving shaft and located at adjacent ends of said shafts, said driven shaft having coaxial divergent recesses at the opposite ends thereof;

a larger ball and a smaller ball received in correspondingly larger and smaller ones of said recesses in said ends of said driven shaft, and correspondingly larger and smaller recesses in the adjacent end of s aid driving shaft and in the housing for coacting with said larger and smaller balls to substantially fixedly locate the rotational axis of said driven shaft with respect to the rotational axis of said driving shaft and said housing, said smaller recesses being substantially coaxial, said larger ball being substantially centered at said obtuse angle intersection of said axes of said shafts, such that said larger ball lies in obtusely angled recesses while said smaller ball lies in said substantially coaxial smaller recesses, said means positively driving said driven shaft from said driving shaft circumferentially surrounding said larger ball, in which the larger recesses are frustoconical, said larger ball having a circular line of contact with the wall of each larger recess, the two circular lines of contact being on opposite sides of the ball center, said means positively driving said driven shaft from said driving shaft comprises meshed bevel gears fixed on said adjacent shaft ends, in which the circular lines of contact are broken by gaps between teeth of the bevel gears.

* * * * *

UNITED STATES PATENT AND TRADEMARK OFFICE
CERTIFICATE OF CORRECTION

PATENT NO. : 4 947 942
DATED : August 14, 1990
INVENTOR(S) : Paul S. Lightle et al.

It is certified that error appears in the above-identified patent and that said Letters Patent is hereby corrected as shown below:

Col. 8, line 21; change "in which the side recess is" to
---in which the side of said recess is---.

Co. 9, line 17; change "end of s aid driving shaft" to
---end of said driving shaft---.

Signed and Sealed this

Seventh Day of January, 1992

Attest:

HARRY F. MANBECK, JR.

*Attesting Officer*   *Commissioner of Patents and Trademarks*